US012667702B2

(12) United States Patent
Dant et al.

(10) Patent No.: US 12,667,702 B2
(45) Date of Patent: Jun. 30, 2026

(54) JOINING DISSIMILAR METALS FOR GUIDEWIRE APPLICATIONS

(71) Applicant: Heraeus Medical Components LLC, St. Paul, MN (US)

(72) Inventors: Jack Dant, St. Paul, MN (US); Mark Erie, Chaska, MN (US); David Johnson, Saint Louis Park, MN (US); Trent Birkholz, Excelsior, MN (US); Eric Lundequam, Hopkins, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 456 days.

(21) Appl. No.: 18/234,019

(22) Filed: Aug. 15, 2023

(65) Prior Publication Data

US 2023/0381461 A1 Nov. 30, 2023

Related U.S. Application Data

(62) Division of application No. 16/354,295, filed on Mar. 15, 2019, now abandoned.

(Continued)

(51) Int. Cl.
*A61M 25/09* (2006.01)
*A61L 31/02* (2006.01)

(52) U.S. Cl.
CPC ........... *A61M 25/09* (2013.01); *A61L 31/022* (2013.01); *A61L 2400/16* (2013.01); *A61M 2025/09108* (2013.01); *A61M 2025/09141* (2013.01)

(58) Field of Classification Search
CPC ............ Y10T 29/49865; B23P 11/025; A61M 2025/09108; A61M 2025/09133; A61M 2025/09141; A61M 25/09
See application file for complete search history.

(56) References Cited

U.S. PATENT DOCUMENTS

| | | | | |
|---|---|---|---|---|
| 2,795,989 A | * | 6/1957 | Koenig | F16B 19/1063 29/523 |
| 3,024,300 A | * | 3/1962 | Martin | H01J 5/26 445/44 |

(Continued)

FOREIGN PATENT DOCUMENTS

JP 2003260140 9/2003

OTHER PUBLICATIONS

Pai, P. Frank. (2007). Highly Flexible Structures—Modeling, Computation, and Experimentation—8.2.4 Shape Memory Alloys. American Institute of Aeronautics and Astronautics (AIAA). Retrieved from https://app.knovel.com/hotlink/pdf/id:kt00AAOU4R/highly-flexible-structures/shape-memory-alloys (Year: 2007).*

(Continued)

*Primary Examiner* — Jason L Vaughan
(74) *Attorney, Agent, or Firm* — Dicke, Billig & Czaja, PLLC

(57) ABSTRACT

One aspect is a method of forming a wire, including providing a first wire section comprising a first material, providing a second wire section comprising a second material different from the first material, cooling a joining section that comprises a superelastic material, inserting the first and second wire sections into the joining section, and allowing the joining section to warm such that it compresses on to both the first and second wire section thereby joining them together.

15 Claims, 3 Drawing Sheets

DISTAL END                                            PROXIMAL END

Related U.S. Application Data

(60) Provisional application No. 62/644,085, filed on Mar. 16, 2018.

(56) References Cited

U.S. PATENT DOCUMENTS

| | | | | |
|---|---|---|---|---|
| 3,456,330 A * | 7/1969 | Norcross | .................. | B25D 1/12 |
| | | | | 29/469 |
| 3,466,738 A * | 9/1969 | Mount | ................... | B21D 39/04 |
| | | | | 29/237 |
| 4,261,644 A * | 4/1981 | Giannaris | ............ | G02B 6/3869 |
| | | | | 385/99 |
| 4,309,807 A * | 1/1982 | Hill | ......................... | F16L 47/22 |
| | | | | 29/446 |
| 4,769,897 A * | 9/1988 | Moseman | ............... | F16L 13/14 |
| | | | | 29/525 |
| 5,341,818 A * | 8/1994 | Abrams | ................... | C22F 1/006 |
| | | | | 600/585 |
| 5,365,943 A * | 11/1994 | Jansen | ................... | A61M 25/09 |
| | | | | 600/585 |
| 5,637,089 A | 6/1997 | Abrams et al. | | |
| 5,695,111 A | 12/1997 | Nanis et al. | | |
| 6,001,068 A | 12/1999 | Uchino | | |
| 6,165,292 A | 12/2000 | Abrams et al. | | |
| 6,280,539 B1 | 8/2001 | Abrams et al. | | |
| 6,461,453 B1 | 10/2002 | Abrams et al. | | |
| 6,602,228 B2 | 8/2003 | Nanis et al. | | |
| 6,637,110 B2 * | 10/2003 | Jee | ......................... | F16L 13/004 |
| | | | | 29/445 |
| 6,638,372 B1 | 10/2003 | Abrams et al. | | |
| 6,645,159 B1 | 11/2003 | Burkett | | |
| 6,682,608 B2 | 1/2004 | Abrams et al. | | |
| 6,866,642 B2 * | 3/2005 | Kellerman | .............. | B21F 15/08 |
| | | | | 600/585 |
| 6,918,882 B2 * | 7/2005 | Skujins | ................. | A61L 31/022 |
| | | | | 604/533 |
| 7,074,197 B2 * | 7/2006 | Reynolds | .............. | A61L 31/022 |
| | | | | 600/585 |
| 7,153,277 B2 * | 12/2006 | Skujins | ................. | A61M 25/09 |
| | | | | 600/585 |
| 7,244,319 B2 | 7/2007 | Abrams et al. | | |
| 7,258,753 B2 | 8/2007 | Abrams et al. | | |
| 7,731,669 B2 * | 6/2010 | Mathews | .............. | A61M 25/09 |
| | | | | 403/333 |
| 7,871,414 B2 * | 1/2011 | Hardin, Jr. | ............ | A61M 25/09 |
| | | | | 604/93.01 |
| 8,487,210 B2 | 7/2013 | Specht et al. | | |
| 9,528,537 B2 * | 12/2016 | Gainor | .................... | F16B 4/008 |
| 2003/0120181 A1 | 6/2003 | Toma | | |
| 2004/0102720 A1 | 5/2004 | Kelleman | | |
| 2004/0167440 A1 | 8/2004 | Sharrow | | |
| 2004/0167441 A1 * | 8/2004 | Reynolds | .............. | A61M 25/09 |
| | | | | 600/585 |
| 2004/0254450 A1 | 12/2004 | Griffin | | |
| 2005/0137614 A1 * | 6/2005 | Porter | ................. | A61M 60/205 |
| | | | | 606/153 |
| 2006/0047223 A1 | 3/2006 | Grandfield | | |
| 2007/0287955 A1 | 12/2007 | Layman | | |
| 2008/0097247 A1 | 4/2008 | Eskuri | | |
| 2008/0183182 A1 | 7/2008 | Satou | | |
| 2009/0227902 A1 | 9/2009 | Simpson | | |
| 2010/0174246 A1 | 7/2010 | Bunch | | |
| 2015/0094616 A1 | 4/2015 | Simpson | | |
| 2015/0094690 A1 | 4/2015 | Simpson | | |
| 2015/0148706 A1 | 5/2015 | Abner | | |
| 2015/0314109 A1 * | 11/2015 | Minar | ............ | A61M 25/09033 |
| | | | | 604/528 |
| 2016/0136396 A1 | 5/2016 | Chludzinski | | |
| 2016/0303353 A1 | 10/2016 | Simpson | | |
| 2017/0239450 A1 | 8/2017 | Kocaturk | | |
| 2018/0092651 A1 | 4/2018 | Terashi | | |
| 2018/0104441 A1 | 4/2018 | Roeger | | |
| 2018/0256860 A1 * | 9/2018 | Minar | ................... | A61M 25/09 |
| 2019/0282787 A1 | 9/2019 | Dant | | |

OTHER PUBLICATIONS

Frank, 8.2.4 Shape Memory Alloys; Highly Flexible Structures pp. 669-711 (Year: 2007).*

Non-Final Office Action dated Apr. 20, 2021 in U.S. Appl. No. 16/354,295.

Final Office Action dated Sep. 28, 2021 in U.S. Appl. No. 16/354,295.

Non-Final Office Action dated Feb. 24, 2022 in U.S. Appl. No. 16/354,295.

Final Office Action dated Aug. 2, 2022 in U.S. Appl. No. 16/354,295.

Non-Final Office Action dated May 15, 2023 in U.S. Appl. No. 16/354,295.

* cited by examiner

DETAIL A

JOINING DISSIMILAR METALS FOR GUIDEWIRE APPLICATIONS

CROSS-REFERENCE TO RELATED APPLICATION

This Non-Provisional Patent Application is a divisional application of U.S. Ser. No. 16/354,295, filed Mar. 15, 2019 which claims the benefit of the filing date of U.S. Provisional Patent Application Ser. No. 62/644,085, filed Mar. 16, 2018, ENTITLED "JOINING DISSIMILAR METALS FOR GUIDEWIRE APPLICATIONS," which is incorporated herein by reference.

TECHNICAL FIELD

One aspect relates to joined dissimilar materials. In one embodiment, the joined materials form a guide wire configured for intravascular use.

BACKGROUND

Intravascular guidewires are used in conjunction with intravascular devices such as catheters to facilitate navigation through the vasculature of a patient. Such guidewires are typically very small in diameter. In some applications, a guidewire can have multiple sections that are joined together in order to form a single wire. Joining sections of such a wire having a small diameter can be challenging, particularly where the sections being joined are configured of different materials. Because there are limitations to many present approaches, there is a need for the present invention.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
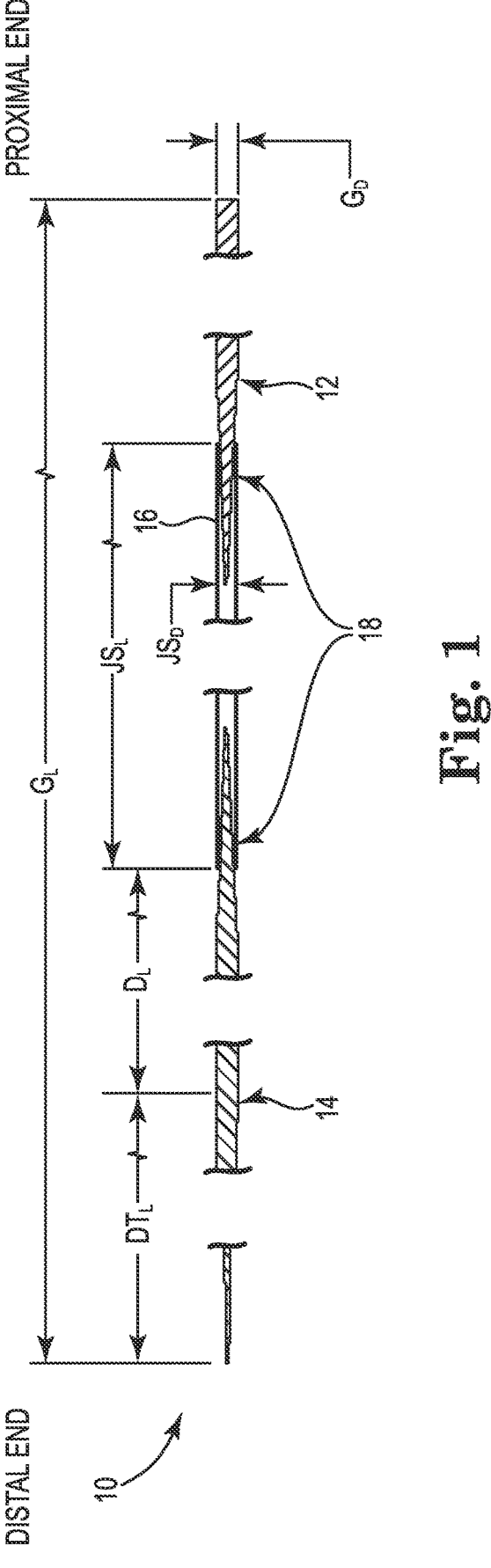
FIG. 1 illustrates a sectional view of joined dissimilar materials in accordance with one embodiment.

FIG. 1 illustrates a guidewire 10 in accordance with one embodiment. In one embodiment, guidewire 10 has a proximal section 12, a distal section 14 and a joining section 16. In one case, proximal, distal and joining sections 12 and 14 are each configured of separate wire segments that are joined together at joining section 16. In some embodiments, proximal and distal sections 12 and 14 are adapted with differing diameter regions, are adapted and configured to obtain a transition in stiffness, and provide a desired flexibility characteristic. In FIG. 1, guidewire 10 is illustrated with a truncation in its ends, as its length may vary in accordance with particular applications.

As used herein, the proximal section 12 and the distal section 14 can generically refer to any two adjacent wire sections along any portion of guidewire 10. Furthermore, although discussed with specific reference to guidewires, the wire segments can be applicable to almost any intravascular device. For example, they are applicable to hypotube shafts for drive shafts for intravascular rotational devices (atherectomy catheters, IVUS catheters, etc.). Such devices may be useful in clinical applications including, but not limited to, interventional oncology, electrophysiology, peripheral, cardiac, urology, neurology, and gastroenterology.

In one embodiment, proximal section 12 is configured of a relatively stiff material, such as stainless steel wire, CoCr alloy or other stiff alloy. In one embodiment, proximal section 12 has a material selected to be relatively stiff for pushability and torqueability.

In some embodiments, distal section 14 is configured of a relatively flexible material, such as a super elastic or linear elastic alloy, wire, such as linear elastic nickel-titanium (NiTi), nickel-titanium alloy, nickel-chromium alloy, nickel-chromium-iron alloy, nickel-titanium-cobalt alloy, or other suitable material, or alternatively, a polymer material, such as a high performance polymer. In one embodiment, the material used to configure distal section 14 can be selected to be relatively flexible for trackability and kink resistance.

In one embodiment, proximal section 12 and the distal section 14 are separate pieces that are joined together with joining section 16. In one embodiment, joining section 16 is a hypotube configured to receive proximal section 12 and the distal section 14 at each of its ends to forms joints 18. In one embodiment, proximal section 12 has a taper at its distal end that is configured to fit into joining section 16 at joint 18. Similarly, distal section 14 has a taper at its proximal end that is configured to fit into joining section 16 at joint 18.

In one embodiment, an adhesive, such as UV Cure, heat cure, Cyanoacrylate, etc., is placed in or adjacent joining section 16 before proximal section 12 and distal section 14 are inserted in order to secure them at joints 18. In one embodiment, proximal section 12 and distal section 14 are secured in joining section 16 with solder, weld or other similar securing method(s). In one embodiment, joining section 16 is a Nitinol alloy hypotube. In other embodiments, similar alloy materials, or materials that are relatively compatible with the materials used for proximal section 12 and distal section 14 can be used for joining section 16.

In various embodiments, the adjoining tapered sections of proximal section 12 and distal section 14 may or may not meet or overlap each other within joining section 16. In one embodiment, average results for tensile-to-fail testing for 0.014 guidewires ranges from 6.9 to 9.1 lbf, depending upon configuration.

In one embodiment, guidewire 10 is configured for intravascular use and can be used in conjunction with intravascular devices such as catheters to facilitate navigation through the vasculature of a patient. Guidewire 10 can embody a range of dimensions that are considered as appropriate for various embodiments. In one embodiment, its outer diameter $G_D$ ranges from about 0.005 to about 0.04 inches. Guidewire 10 is configured in a variety of lengths, and in one embodiment, its overall length $G_L$ ranges from about 6.0 to about 140.0 inches. In one embodiment, the length of the distal taper $DT_L$ on distal section 14 ranges from 0.5 to 12.0 inches. In one embodiment, outside the distal taper, the distal length $D_L$ of the distal section 14 is from 0.25 to 20.0 inches. In one embodiment, the length $JS_L$ of joining section 16 is from 0.5 to 4.0 inches, while the diameter $JS_D$ of joining section 16 is from 0.005 to 0.04 inches.

Figures 2A, 2B:
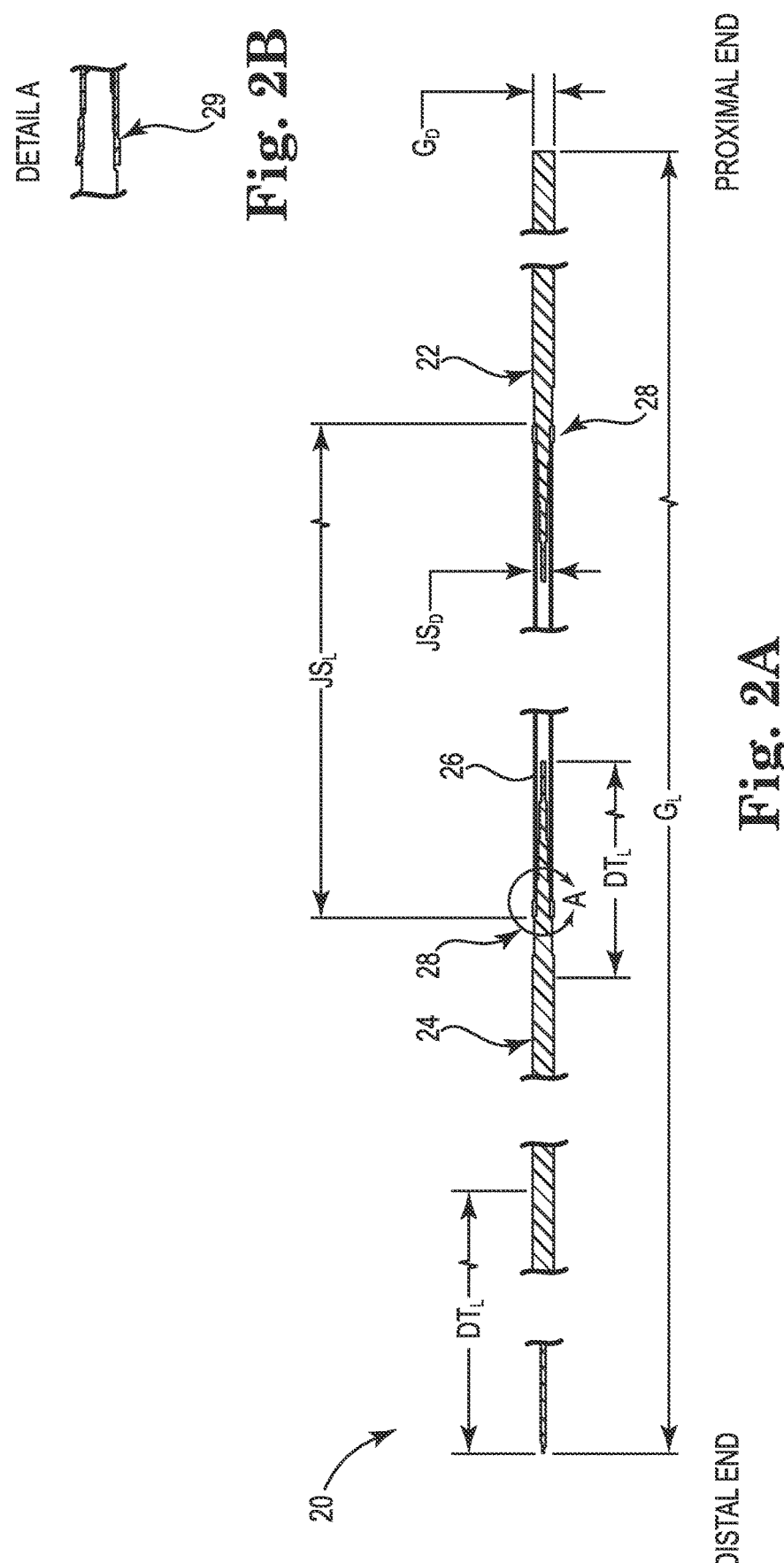
FIG. 2A illustrates a sectional view of joined dissimilar materials in accordance with one embodiment.
FIG. 2B illustrates an enlarged view of the section from FIG. 2A in accordance with one embodiment.

FIG. 2A illustrates a guidewire 20 in accordance with one embodiment. In one embodiment, guidewire 20 has a proximal section 22, a distal section 24 and a joining section 26. In one case, proximal, distal and joining sections 22 and 24 are each configured of separate wire segments that are joined together at joining section 26. In some embodiments, proximal and distal sections 22 and 24 are adapted with differing diameter regions, are adapted and configured to obtain a transition in stiffness, and provide a desired flexibility characteristic. In FIG. 2A, guidewire 20 is illustrated with a truncation in its ends, as its length may vary in accordance with particular applications.

As used herein, the proximal section 22 and the distal section 24 can generically refer to any two adjacent wire sections along any portion of guidewire 20. Furthermore, although discussed with specific reference to guidewires, the wire segments can be applicable to almost any intravascular device. For example, they are applicable to hypotube shafts for drive shafts for intravascular rotational devices (atherectomy catheters, IVUS catheters, etc.). Such devices may be useful in clinical applications including, but not limited to, interventional oncology, electrophysiology, peripheral, cardiac, urology, neurology, and gastroenterology.

In one embodiment, proximal section 22 is configured of a relatively stiff material, such as stainless steel wire, CoCr alloy or other stiff alloy. In one embodiment, proximal section 22 has a material selected to be relatively stiff for pushability and torqueability.

In some embodiments, distal section 24 is configured of a relatively flexible material, such as a super elastic or linear elastic alloy, wire, such as linear elastic nickel-titanium (NiTi), nickel-titanium alloy, nickel-chromium alloy, nickel-chromium-iron alloy, nickel-titanium-cobalt alloy, or other suitable material, or alternatively, a polymer material, such as a high performance polymer. In one embodiment, the material used to configure distal section 24 can be selected to be relatively flexible for trackability.

In one embodiment, proximal section 22 and the distal section 24 are separate pieces that are joined together with joining section 26. In one embodiment, joining section 26 is a hypotube configured to receive proximal section 22 and the distal section 24 at each of its ends to forms joints 28. In one embodiment, proximal section 22 has a taper at its distal end that is configured to fit into joining section 26 at joint 28. Similarly, distal section 24 has a taper at its proximal end that is configured to fit into joining section 26 at joint 28.

In one embodiment, proximal section 22 and distal section 24 are coupled with joining section 26 via a cold press process, whereby joining section 26 is forcibly assembled to the two other sections. In one embodiment, before proximal section 22 and distal section 24 are inserted, joining section 26 is thermally cooled below 32° F., followed by the immediate, forceful insertion of proximal and distal sections 22, 24 into the joining section 26, such that a flaring deformation occurs on both ends of joining section 26. Next, all the joined sections are warmed to room temperature, or about 70° F., at which point the joining section 26 attempts to return to its pre-formed configuration, thereby creating a compressive force on the proximal and distal sections 22, 24.

FIG. 2B, illustrates further detail of detail area A in FIG. 2A, illustrating a flare 29 in joining section 26 at joint 28 that results from the cold press process. This compressive force holds the components such that the assembly resists disassociation when acted upon by opposing tensile forces along the longitudinal axis.

In various embodiments, the adjoining tapered sections of proximal section 22 and distal section 24 may or may not meet or overlap each other within joining section 26. In one embodiment, average results for tensile-to-fail testing for 0.018 inch guidewires incorporating this type of connection is 3.1 lbf. In one embodiment, joining section 26 is a Nitinol alloy hypotube. In other embodiments, similar alloy materials can be used for joining section 26.

In one embodiment, guidewire 20 is configured for intravascular use and can be used in conjunction with intravascular devices such as catheters to facilitate navigation through the vasculature of a patient. Guidewire 20 can embody a range of dimensions that are considered as appropriate for various embodiments. In one embodiment, its outer diameter $G_D$ ranges from about 0.005 to about 0.04 inches. Guidewire 20 is configured in a variety of lengths, and in one embodiment, its overall length $G_L$ ranges from about 6.0 to about 140.0 inches. In one embodiment, the length of the distal taper $DT_L$ on distal section 24 ranges from 0.5 to 12.0 inches. In one embodiment, outside the distal taper, the distal length $D_L$ of the distal section 24 is from 0.25 to 20.0 inches. In one embodiment, the length $JS_L$ of joining section 26 is from 0.5 to 4.0 inches, while the diameter $JS_D$ of joining section 26 is from 0.005 to 0.04 inches. In one embodiment, the length $DT_L$ of the distal taper of the distal section 24 extending into joining section 26, is from 0.25 to 1.5 inches.

Figure 3:
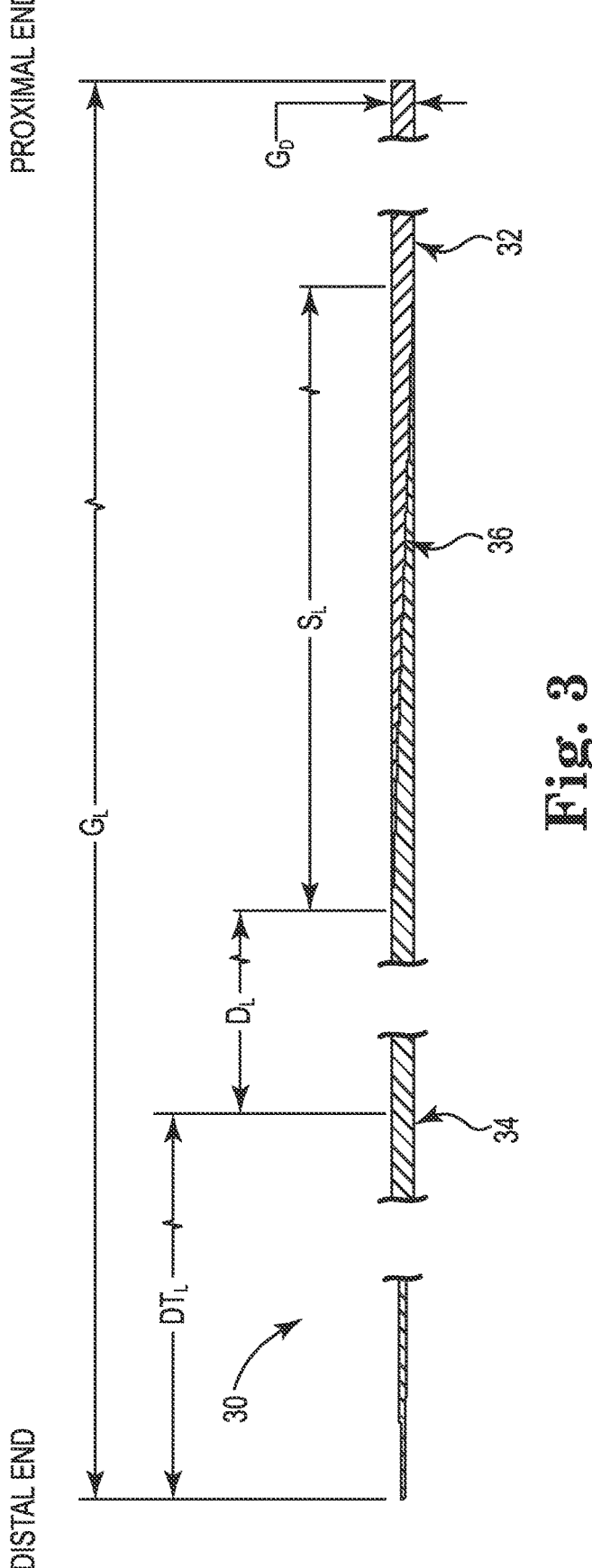
FIG. 3 illustrates a sectional view of joined dissimilar materials in accordance with one embodiment.

FIG. 3 illustrates a guidewire 30 in accordance with one embodiment. In one embodiment, guidewire 30 has a proximal section 32, a distal section 34 and a joining section 36. In one case, proximal, distal and joining sections 32 and 34 are each configured of separate wire segments that are joined together at joining section 36. In some embodiments, proximal and distal sections 32 and 34 are adapted with differing diameter regions, are adapted and configured to obtain a transition in stiffness, and provide a desired flexibility characteristic. In FIG. 3, guidewire 30 is illustrated with a truncation in its ends, as its length may vary in accordance with particular applications.

As used herein, the proximal section 32 and the distal section 34 can generically refer to any two adjacent wire sections along any portion of guidewire 30. Furthermore, although discussed with specific reference to guidewires, the wire segments can be applicable to almost any intravascular device. For example, they are applicable to hypotube shafts for drive shafts for intravascular rotational devices (atherectomy catheters, IVUS catheters, etc.). Such devices may be useful in clinical applications including, but not limited to, interventional oncology, electrophysiology, peripheral, cardiac, urology, neurology, and gastroenterology.

In one embodiment, proximal section 32 is configured of a relatively stiff material, such as stainless steel wire, CoCr alloy or other stiff alloy. In one embodiment, proximal section 32 has a material selected to be relatively stiff for pushability and torqueability.

In some embodiments, distal section 34 is configured of a relatively flexible material, such as a super elastic or linear elastic alloy, wire, such as linear elastic nickel-titanium (NiTi), nickel-titanium alloy, nickel-chromium alloy, nickel-chromium-iron alloy, nickel-titanium-cobalt alloy, or other suitable material, or alternatively, a polymer material, such as a high performance polymer. In one embodiment, the material used to configure distal section 34 can be selected to be relatively flexible for trackability.

In one embodiment, proximal section 32 and the distal section 34 are separate pieces that are joined together at joining section 36. In one embodiment, proximal section 32 has a flat grind taper at its distal end, while distal section 34 has a flat grind taper at its proximal end that is complementary or a mirror image of the flat grind on proximal section 32. As such, joining section 36 "scarf joint" with the two tapered portions joined together. In one embodiment, the two surfaces of the taper joint have a diagonally cut or ground mating surface. In one embodiment, the tapers are configured such that, when joined at joining section 36, the outer diameter of guidewire 30 is constant from both sides of joining section 36, as well as throughout joining section 36. In one embodiment, the taper joint at joining section 36 is a flat diagonal line, while in other embodiments, it has a curved or parabolic shape. In various embodiments, the tapers can be achieved by grinding, machining, stamping, etc., and result in a configuration that, when joined to the mating component, results in an approximate restoration of the original component diameter.

In one embodiment, the tapered portions of proximal section 32 and distal section 34 are coupled at joining section 36 using a variety of methods. The mating surfaces can be secured together using solder, adhesive (UV Cure, heat cure, Cyanoacrylate, etc.), welding, etc., such that a secure, flexible bond is created between the two mating components. Following the assembly, the resulting assembly may be further ground, machined, etc. to create a smooth outer diameter, covered (with a polymer, heat shrink, coil, braid or other component) to further secure the joint and/or modify the assembly handling characteristics. Average results for tensile-to-fail testing for 0.014 guidewires with this type of connection is 7.3 lbf. FIG. 3 also includes a range of dimensions that could be considered as appropriate for the given features in some embodiments.

In one embodiment, guidewire 30 is configured for intravascular use and can be used in conjunction with intravascular devices such as catheters to facilitate navigation through the vasculature of a patient. Guidewire 30 can embody a range of dimensions that are considered as appropriate for various embodiments. In one embodiment, its outer diameter $G_D$ ranges from about 0.005 to about 0.04 inches. Guidewire 30 is configured in a variety of lengths, and in one embodiment, its overall length $G_L$ ranges from about 6.0 to about 140.0 inches. In one embodiment, the length of the distal taper $DT_L$ on distal section 34 ranges from 0.5 to 12.0 inches. In one embodiment, outside the distal taper, the distal length $D_L$ of the distal section 34 is from 0.25 to 20.0 inches. In one embodiment, the length $JS_L$ of joining section 36 is from 0.25 to 1.5 inches.

With any of the above-described embodiments, dissimilar metals are joined together for use in guidewire applications. In many embodiments, the joining of a proximal component of relatively high stiffness (stainless steel, cobalt chromium, etc.) with a distal section that is relatively more flexible and resists kinking, manufactured from a material with superelastic properties (Nitinol, NiTiCo, etc.), provides useful characteristics for many guidewire applications.

With any of the above-described embodiments, one or more coils may be added to the distal end of the distal sections, which can be tapered at the distal end to receive such coil(s). Furthermore, any of the above-described embodiments can partially or fully be covered by a polymer jacket. Also, portions of any of the guidewires that have superelastic properties, e.g., Nitinol, NiTiCo, etc., can be annealed or semi-annealed, so that those portions can have a bend or kink introduced, which may be favorable feature in some applications.

The described joining structures and methods can be employed mid-shaft on a guidewire, more proximally or more distally as dictated by the specific requirements of the applications. Additionally, the connections may occur on a portion of the guidewire that has a shaft diameter that is reduced from the primary shaft diameter (e.g., a step-down portion of the distal tip) or on a tapered section of the guidewire.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A method of forming a medical guidewire comprising:
   providing a first wire section comprising a first material;
   providing a second wire section comprising a second material different from the first material;
   providing a joining section that comprises a superelastic material and has first and second ends;
   cooling the joining section;
   after cooling the joining section, forcefully inserting the first wire section into the first end of the joining section and forcibly inserting the second wire section into the second end of the joining section;
   after inserting the wire sections, warming the joining section such that it compresses on to both the first and second wire sections thereby joining them together as the guidewire;
   wherein forcefully inserting the first and second wire sections into the joining section causes a flaring deformation at each of the first and second ends of the joining section.

2. The method of claim 1, wherein warming the joining section causes the joining section to apply a compressive force on each first and second wire sections.

3. The method of claim 1, wherein the first material comprising one of stainless steel, nickel-chromium alloy, nickel-chromium-iron alloy, and cobalt alloy and wherein the second material comprising nickel-titanium.

4. The method of claim 1, wherein cooling the joining section comprises cooling the joining section to a temperature below 32° F.

5. The method of claim 1, wherein warming the joining section comprises warming the joining section to at least 70° F.

6. The method of claim 1, wherein the joining section comprises a Nitinol alloy.

7. The method of claim 1, wherein the guidewire has an outer diameter of between 0.005 and about 0.04 inches.

8. The method of claim 1, wherein the guidewire has average results for tensile-to-fail testing of connection is at least 3.1 lbf.

9. A method of forming a guidewire comprising:
   providing a first wire section comprising a first material;

providing a second wire section comprising a second material different from the first material;

cooling a joining section that comprises a superelastic material;

inserting the first and second wire sections into the joining section;

allowing the joining section to warm such that it compresses on to both the first and second wire section thereby joining them together;

wherein inserting the first and second wire sections into the joining section causes a flaring deformation at each of a first and a second end of the joining section.

10. The method of claim 9, wherein allowing the joining section to warm causes the joining section to apply a compressive force on each first and second wire sections.

11. The method of claim 9, wherein the first material comprising one of stainless steel, nickel-chromium alloy, nickel-chromium-iron alloy, and cobalt alloy and wherein the second material comprising nickel-titanium.

12. The method of claim 9, wherein cooling the joining section comprises cooling to a temperature below 32° F., and wherein allowing the joining section to warm comprises warming to room temperature.

13. The method of claim 9, wherein the joining section comprises a Nitinol alloy.

14. The method of claim 9, wherein the guidewire has an outer diameter of between 0.005 and about 0.04 inches.

15. The method of claim 9, wherein the guidewire has average results for tensile-to-fail testing of connection is at least 3.1 lbf.

* * * * *